(12) United States Patent
Katz et al.

(10) Patent No.: US 7,250,252 B2
(45) Date of Patent: Jul. 31, 2007

(54) AMPLIFICATION BASED POLYMORPHISM DETECTION

(76) Inventors: David Aaron Katz, 936 Hinman, Evanston, IL (US) 60202; Maria C. Gentile-Davey, 10025 39th Ave., Pleasant Prairie, WI (US) 53158-6502

(*) Notice: Subject to any disclaimer, the term of this patent is extended or adjusted under 35 U.S.C. 154(b) by 11 days.

(21) Appl. No.: 09/747,538

(22) Filed: Dec. 21, 2000

(65) Prior Publication Data
US 2002/0102549 A1    Aug. 1, 2002

Related U.S. Application Data

(60) Provisional application No. 60/173,699, filed on Dec. 30, 1999.

(51) Int. Cl.
C12Q 1/68       (2006.01)
C12P 19/34      (2006.01)
C07H 21/04      (2006.01)

(52) U.S. Cl. .................. 435/6; 435/91.2; 536/24.31; 536/24.32; 536/24.33

(58) Field of Classification Search .............. 435/6, 435/91.2; 536/24.32, 24.33, 24.31
See application file for complete search history.

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 5,210,015 A | 5/1993 | Gelfand et al. | 435/6 |
| 5,399,491 A | 3/1995 | Kacian et al. | 435/91.21 |
| 5,424,414 A | 6/1995 | Mattingly | 536/25.32 |
| 5,464,764 A | 11/1995 | Capecchi et al. | 435/172.3 |
| 5,582,989 A | 12/1996 | Caskey et al. | 435/6 |
| 5,648,482 A * | 7/1997 | Meyer | 536/24.33 |
| 5,792,607 A | 8/1998 | Backman et al. | 435/6 |
| 5,925,517 A | 7/1999 | Tyagi et al. | 435/6 |
| 6,143,529 A * | 11/2000 | Lapidus et al. | 435/91.2 |
| 6,232,079 B1 * | 5/2001 | Wittwer et al. | 435/6 |
| 6,361,940 B1 * | 3/2002 | Van Ness et al. | 435/6 |

FOREIGN PATENT DOCUMENTS

| | | |
|---|---|---|
| EP | 320308 | 6/1989 |
| EP | 463395 | 1/1992 |
| WO | 9732040 | 9/1997 |
| WO | 9848052 | 10/1998 |
| WO | WO 98/48052 | * 10/1998 |

OTHER PUBLICATIONS

Johansson I et al. PCR-based genotyping for duplicated and deleted CYP2D6 genes. Pharmacogenetics, vol. 6, pp. 351-355, 1996.*
Labuda D et al. Rapid detection of CYP1A1, CYP2D6, and NAT variants by multiplex polymerase chain reaction and allel-specific oligonucleotide assay. Anal Biochem., vol. 275, pp. 84-92, 1999.*
Johansson et al. PCR-based genotyping for duplicated and deleted CYP2D6 genes. Pharmacogenetics, vol. 6, pp. 351-355, 1996.*
Evans et al. Genetic basis for a lower prevalence of deficient CYP2D6 oxidtive drug metabolism phenotypes in Black Americans. J. Clin. Invest., vol. 91, pp. 2150-2154, 1993.*
Steen et al. Detection of the poor metabolizer-associated CYP2D6(D) gene deletion allele by long-PCR technology. Pharmacogenetics, vol. 5, pp. 215-223, 1995.*
Daly, AK, Steen, VM, Fairborther, KS, and Idle, JR; Methods in Enzymology, vol. 22, Chapter 22 (1996).
Wang, S-L, Huang, J-D, Lai, M- D, Lui, B-H, and Lai, M -L; Clinical Pharmacology and Therapeutics, vol. 53, pp. 410-418 (1993).
Wetmur, J. G.; Critical Reviews in Biochemistry and Molecular Biology; vol. 26, pp. 227-259 (1991).
Jou, Cynthia, et al., Amplification Based Mutation Detection; 08/844,275—PCT/US98/07909.
Johansson, I., et al., "PCR-based genotyping for duplicated and deleted *CYP2D6* genes", *Pharmacogenetics*, 6:351-355 (1996).
Roberts, R., et al., "Rapid and Comprehensive Determination of Cytochrome P450 *CYP2D6* Poor Metabolizer Genotypes by Multiplex Polymerase Chain Reaction", *Human Mutation*, 16:77-85 (2000).
Stüven, T., et al., "Rapid detection of *CYP2D6* null alleles by long distance- and multiplex-polymerase chain reaction", *Pharmacogenetics*, 6:417-421 (1996).

* cited by examiner

*Primary Examiner*—Suryaprabha Chunduru

(57) ABSTRACT

An improved method of amplifying nucleic acids comprising the use of four discrete temperature steps in a thermocyclic amplification reaction, as well as, a method of detecting large nucleic acid insertions or deletions such as those that occur from gene duplication or deletion.

6 Claims, No Drawings

AMPLIFICATION BASED POLYMORPHISM DETECTION

This is a conversion of U.S. Provisional Application No. 60/173,699 filed Dec. 30, 1999.

TECHNICAL FIELD

The present invention relates to nucleic acid polymorphisms and, in particular, relates to analyzing polymorphisms using nucleic acid amplification technology.

BACKGROUND OF THE INVENTION

Studies designed to determine the sequence of the human genome, as well as studies designed to compare human genomic sequences, have elicited information regarding polymorphisms of such sequences. A wide variety of polymorphisms in the human genome have previously been described. The various types of human genetic polymorphisms include single base substitutions, insertions, or deletions; variable numbers of tandem repeats; deletions of all or a large part of a gene; gene amplifications; and chromosomal rearrangements.

Cytochrome P450 (CYP) is a family, or group, of genes in the human genome that encode enzymes several of which facilitate the metabolism of various drugs. One of these genes, CYP2D6, plays a role in the metabolism of a large number of drugs, including several products used to treat psychiatric and cardiovascular disorders. Not surprisingly therefore, some variants of CYP2D6 have been found, at least in part, to alter an individual's ability to metabolize drugs.

While some CYP2D6 polymorphisms have little effect on an individual's ability to metabolize drugs, others have a significant effect. For example, a variant known as CYP2D6 star five (CYP2D6*5, hereinafter *5) comprises a deletion of most of the CYP2D6 gene. *5 is one of several CYP2D6 variants that can contribute to a poor metabolizer phenotype, characteristic of persons having an at least impaired ability to metabolize certain classes of drugs. A possible consequence of the poor metabolizer phenotype is that drugs, normally metabolized by CYP2D6, may build up to toxic concentrations in poor metabolizer individuals. Alternatively, a drug requiring activation by CYP2D6 protein may not be efficacious in persons having the poor metabolizer phenotype. Other variants that can contribute to a poor metabolizer phenotype include a single nucleotide substitution (CYP2D6 star 4 or CYP2D6*4, herenafter *4) and two single nucleotide deletions (CYP2D6 star 3 or CYP2D6*3 hereinafter *3; and CYP2D6 star 6 or CYP2D6*6 hereinafter *6).

On the other hand, some individuals carry multiple copies of the CYP2D6 gene (variously referred to as "an amplification" of the CYP2D6 gene or CYP2D6×2, hereinafter ×2) in their genomes. Individuals with this variant may have an increased ability to metabolize certain classes of drugs and therefore normal doses of these drugs are cleared from the body quite quickly and have little chance to achieve the desired effect. Other variants of CYP2D6 including CYP2D6 star 2 (CYP2D6*2 hereinafter *2), a single nucleotide substitution, and CYP2D6 star 9 (CYP2D6*9 hereinafter *9), a three nucleotide deletion, have not been demonstrated to have any affect on an individual's ability to metabolize drugs. Hence, there are various and different types of CYP2D6 variants that may or may not impair drug metabolism in humans.

Many different methods have been proposed to detect variants such as those mentioned above. Unfortunately, however, different detection methodologies have previously appeared necessary to detect different types of variants. While nucleic acid amplification based assays for single nucleotide polymorphisms have used technology that is amenable to automation, amplification based assays for detecting larger variations such as large deletions or insertions are not readily amenable to automation. For example, "allele specific PCR" is described in European Patent Application 463 395 and is a method for detecting single nucleotide polymorphisms. Allele specific PCR based assays can be performed using methodologies that are relatively easy to automate. On the other hand, "long PCR" has been employed to detect large insertions or deletions of nucleic acid sequences, particularly *5 and ×2 (Johansson I., Lundqvist E., Dahl M. L., and Ingelman-Sundberg, *Pharmacogenomics*, 6, 351–355 (1996). While amplification products from allele specific PCR and long PCR can be detected on gels, long PCR products are somewhat limited to gel detection. Accordingly, current methodologies require the use of gels to detect certain types of mutations.

It is well known, however, that running gels is time consuming and therefore expensive. Moreover, there is no single platform that enables the detection of, for example, single base polymorphisms and large deletions using a single format that is readily amenable to automation. Accordingly, there is a need for means to detect amplification products from multiple and different types of polymorphisms on a single automated platform.

BRIEF DESCRIPTION OF THE INVENTION

Provided herein are methods capable of analyzing polymorphic nucleic acid sequences in a manner suitable for automation. The methods are particularly suited for detecting nucleic acid sequences having a variant which is a large deletion or insertion. Typically, such variations will be on the order of fifty nucleotides or more. Advantageously, the methods for detecting such variant nucleic acid sequences are readily amenable to automation and are readily incorporated into a panel of assays analyzing multiple types of genetic polymorphisms.

According to one method, the presence of a deletion or an insertion in a target nucleic acid sequence in a test sample comprises the steps of: a) contacting the test sample with amplification reagents and a set of amplification primers to form a reaction mixture wherein the set of amplification primers hybridize with the target nucleic acid sequence and a standard nucleic acid sequence in the test sample; b) subjecting the reaction mixture to amplification conditions to form a target nucleic acid sequence amplification product and a standard nucleic acid amplification product; c)hybridizing a first probe to the target sequence amplification product and a second probe to the standard nucleic acid sequence amplification product to form first probe/target sequence amplification product hybrids and second probe/standard nucleic acid amplification product hybrids; d) detecting the hybrids; and e) comparing the signals from the first and second labeled probes to determine the presence of the deletion or insertion in the target nucleic acid sequence in the test sample.

DETAILED DESCRIPTION OF THE INVENTION

So-called "large variants" such as multiple base deletions or insertions can be detected in accordance with the methods herein provided using nucleic acid amplification technology. Moreover, the methods for detecting such variations employ techniques that do not require the use of, for example, gels and are therefore readily amenable to automation. As a result, assays for large variants can now be performed on an automated system that also can be used for detecting "smaller variants" such as single nucleotide polymorphisms.

Generally, the methods for detecting large variations in a nucleic acid sequence in a test sample rely upon the specificity of amplification primers employed to amplify such sequences and/or the specificity of hybridization probes employed to detect products of an amplification reaction. These methods can be applied in amplification reactions well known in the art that employ relatively short nucleic acid sequences (or "primers") and amplification reagents to prime synthesis of multiple copies of a target sequence in a test sample. Nucleic acid amplification reactions are, by now, well known and examples of amplification reactions that can be employed in accordance with methods provided herein include LCR described in European Patent Number 320 308 and its variations, such as gap LCR described in U.S. Pat. No. 5,792,607 (herein incorporated by reference), NASBA or similar reactions such as TMA described in U.S. Pat. No. 5,399, 491 (herein incorporated by reference), Invader assays using for example a "cleavase" enzyme and preferably PCR which is described in U.S. Pat. Nos. 4,683, 195 and 4,683,202 (both of which are herein incorporated by reference).

The phrase "amplification reaction reagents" as used herein means reagents which are well known for their use in nucleic acid amplification reactions and may include but are not limited to: a single or multiple reagent, reagents, enzyme or enzymes separately or individually having reverse transcriptase, polymerase, and/or ligase activity; enzyme cofactors such as magnesium or manganese; salts; nicotinamide adenine dinucleotide (NAD); and deoxynucleoside triphosphates (dNTPs) such as, for example, deoxyadenosine triphosphate, deoxyguanosine triphosphate, deoxycytodine triphosphate and thymidine triphosphate. The exact amplification reagents employed are largely a matter of choice for one skilled in the art based upon the particular amplification reaction employed.

The term "test sample" as used herein means anything suspected of containing a "target sequence" which is a sequence that is amplified or detected using the methods provided herein. A "putative sequence" or "putative target sequence" as used herein is a target sequence that contains or is suspected of containing a variant version of the target sequence. The test sample is or can be derived from any source, such as for example, biological sources including blood, plasma, ocular lens fluid, cerebral spinal fluid, milk, ascites fluid, synovial fluid, peritoneal fluid, amniotic fluid, tissue, fermentation broths, cell cultures, products of an amplification reaction, nucleic acid synthesis products and the like. Test samples can also be from, for example, environmental or forensic sources including sewage or cloth. The test sample can be used directly as obtained from the source or following a pre-treatment to modify the character of the sample. Thus, the test sample can be pre-treated prior to use by, for example, preparing plasma from blood, isolating cells from biological fluids, homogenizing tissue, disrupting cells or viral particles, preparing liquids from solid materials, diluting viscous fluids, filtering liquids, distilling liquids, concentrating liquids, inactivating interfering components, adding reagents, purifying nucleic acids, and the like.

According to one embodiment for detecting large deletions or insertions, primer sequences are selected such that they will hybridize and prime amplification of a sequence that does not contain a large deletion, but will not amplify the same sequence when it contains that large deletion. A "large deletion" generally refers to a deletion of eight or more consecutive nucleotides, and preferably fifty or more consecutive nucleotides, most preferably two-hundred or more nucleotides, from a nucleic acid sequence. In accordance with this embodiment, when the large deletion is present, the site where the primer would otherwise bind is absent from the target sequence. Preferably, the primer-binding site is completely missing from the target sequence when the large deletion is present. Accordingly, when a reaction mixture comprising the primer(s), amplification reagents and the test sample is formed and subjected to amplification conditions, an amplification product will be formed in the absence of the deletion, but not will not be formed in cases where the deletion is present. "Primer" as used herein is given its ordinary meaning and typically is a short nucleic acid sequences (a.k.a. an oligonucleotide) typically at least eight nucleotides long, preferably at least ten nucleotides long, and more preferably between ten and one-hundred nucleotides long.

The term "amplification conditions" as used herein means conditions that support annealing and extension of primer sequences. As is known in the art amplification conditions vary with the amplification reaction employed. For example, in amplification reactions such as PCR and LCR, raising and lowering the temperature in the environment of the reaction mixture, such as by thermal cycling, are appropriate amplification conditions. In cases where so-called isothermal amplification reactions, such as NASBA or TMA, are employed, raising and lowering the temperature is not continuously required as with PCR or LCR. Amplification conditions for isothermal reactions generally require dissociating double stranded sequences, chemically or with heat to allow primers to bind and amplification to proceed. In any event, amplification conditions are well known and a matter of choice for those skilled in the art based upon the amplification reaction being employed.

A preferred set of amplification conditions include subjecting a reaction mixture to the following cycle: (a) raising the temperature of the reaction mixture to a temperature sufficient to dissociate double stranded nucleic acid sequences, (b) lowering the temperature of the reaction mixture to allow the PCR primers and a probe to hybridize to the nucleic acid and thereby form primer hybrids and probe hybrids, (c) raising the temperature of the reaction mixture to a temperature sufficient to dissociate the probe hybrids, if the probe is not completely complementary to the nucleic acid, but not sufficient to dissociate the primer hybrids, and (d) raising the temperature of the reaction mixture to a temperature sufficient to activate the polymerase. The exact number of times the cycle is repeated will depend on the concentration of the original target sequence in the test sample but preferably the cycle is repeated at least 10 times, more preferably at least 20 times, and most preferably more than 30 times. It will also be understood that the above cycle may also include a step where amplification products are detected after each cycle in a "real time" type manner.

The precise temperatures at which, for example, double stranded nucleic acid sequences dissociate, primers and probes hybridize or dissociate, and polymerase is active, are dependent upon the length and composition of the sequences involved, and the source of the polymerase. With the above factors in mind, however, one skilled in the art can easily determine the most appropriate temperatures for achieving the above functions empirically [See for example, Wetmur, J. G., *Critical Reviews in Biochemistry and Molecular Biology*; 26 pp227–259 (1991)]. It has been found however that, in most cases, temperatures above 90° C., and preferably temperatures between 92° C. and 100° C., are sufficient to dissociate double stranded nucleic acid sequences. Temperatures that are most effective for forming primer hybrids and probe hybrids are typically between 45° C. and 65° C., more typically between 55° C. and 59° C. Temperatures sufficient to dissociate the probe hybrids, if the probe is not completely complementary to the nucleic acid, but not sufficient to dissociate the primer hybrids; include temperatures at least a degree Celsius above the hybrid formation temperature and more typically 2 or more degrees Celsius above the hybrid formation temperature. Thermostable polymerases are typically active at temperatures between 60° C. and 90° C., but are most typically thought to be optimally active at 72° C.

The presence of a large deletion in a nucleic acid sequence also can be detected with a positive signal instead of detecting the presence of a large deletion when no amplification product, and therefore no signal is detected when the large deletion is present, as explained above. For example, primers can be selected such that when the deletion is present the sequences are in close enough proximity to allow the extension product of one primer to serve as a template for another primer. In other words, the extension product of one primer will include a binding site for the other primer. In the absence of the deletion, however the primers will not bind or will bind at sites so distant from one another that the enzyme employed to extend the primers is not capable of performing such function sufficiently to permit effective amplification. Hence, when subjected to amplification conditions, an amplification product will be formed when the deletion is present but not when the deletion is absent. As a result, the amplification product from the sequence containing the deletion can be detected as an indication of such a sequence in the test sample.

Amplification products formed in the manners described above, if any, can be detected and the presence of a detectable signal may indicate the presence or absence of the deletion. To insure that a failure to detect a particular amplification product correlates to the absence of a particular target sequence, and not a result of the inefficacy of the amplification reaction (i.e. amplification reagents and conditions), a control sequence can be employed. Use of a control sequence is particularly advantageous when the failure to detect an amplification product is indicative of the presence of a large deletion.

A control sequence is a target sequence that is added to the reaction mixture, or is known to be present in the reaction mixture, and is amplified when the reaction mixture is subjected to amplification conditions notwithstanding the presence or absence of the large deletion in a nucleic acid sequence. Control sequences that are not added to the reaction mixture, but are otherwise known to be present in the test sample may include, for example, nucleic acid sequences that are consistently present in a genome and not within the region containing the large deletion being assayed. Appropriate primers can also be added to the reaction mixture to amplify the control sequence.

Alternatively, control sequences can be selected such that they use the same primers used to amplify the sequence putatively containing the large deletion, such as by using a pseudogene related to the putative sequence as the control sequence. The control product can be detected to determine that the amplification reaction was efficacious and thereby insure that the failure to detect the target sequence, which could contain the large deletion, is in fact due to the presence of the deletion and not a failure of the amplification reaction. Control sequences can also be employed when the presence of a detectable amplification product indicates the presence of a deletion, to insure that the failure to detect the target sequence is in fact due to the absence of the deletion and not a failure of the amplification reaction.

The presence of a large deletion in a nucleic acid sequence contained in a test sample can also be detected by co-amplifying a second target sequence (or standard sequence) in combination with the sequence putatively containing the large deletion (the putative sequence). Similarly to above, the primer sequences hybridize to a portion of the putative sequence in a region that is absent when the deletion is present and a loss of amplification product is therefore observed in such instances. According to this embodiment, large insertions or gene amplifications also can be detected in a nucleic acid sequence. Large insertions or gene amplifications refers to a phenomenon where a sequence of nucleic acid is repeated, usually tandemly, in a genome. Accordingly, when a large insertion is present, the primer sequences have an increased number of initial target sequences and therefore an increased concentration of amplification product is observed when the large insertion is present. Preferably, insertions of at least fifty base pairs, more preferably, two-hundred base pairs and most preferably one-thousand base pairs are detected using this method.

Hybridization probes specific for the putative sequence and the standard sequence can be employed to detect the amplification products generated for the respective sequences. Signals from signal generating groups present on the primers or probes can then be detected from each of the amplification products. The signals can then be compared. The signal detected from the amplification product of the standard sequence serves as a benchmark for determining whether an amplification or deletion is present. In particular, if the signal from the putative sequence is lower than the signal detected from the standard sequence, a deletion is present in the putative sequence found in the test sample. On the other hand if the signal from the putative sequence is higher than that from the standard sequence, then a gene amplification is present in putative sequence found in the test sample.

Similarly to the control sequence discussed above, the standard sequence can be added to the reaction mixture in concentrations suitable for making the above comparison. Preferably, however, the standard sequence is selected from sequences known to be present in the test sample and known to be present in a particular copy number. Sequences within genes or psuedogenes homologous to the putative sequence have been found to be useful for purposes of acting as a standard sequence. Such examples are particularly attractive standard sequences because primer sequences can be selected such that at least one primer of a set can be employed to amplify both a standard sequence and the putative sequence to thereby reduce the number of reagents employed in an assay. Primer sequences for this purpose can be selected by comparing the sequences of the putative sequence and the standard sequence for suitable primer sites that will amplify both sequences. As it will become evident below, also important in this comparison is selecting a sequence from the homologous gene or pseudogene and the putative sequence that contain at least one common primer site, but also contain at least a one base pair distinction in the sequences between the primer binding sites. Hence, it is most preferable to select a standard sequence from the homologous gene or psuedogene sequence that contains the same primer binding sites as the putative sequence but is divergent from the putative sequence in the region between the primer binding sites.

The amplification products from the putative sequence, if any, and the standard sequence are then detected using probes that are specific for either sequence. In practice, therefore, a reaction mixture is formed by contacting a test sample with amplification reagents and primer sets for amplifying the putative sequence and the standard sequence. The reaction mixture is placed under amplification conditions to form an amplification product from the standard sequence and an amplification product from the putative sequence, in the event it does not contain the large deletion. Probes, specific to the respective amplification products, are then hybridized to the amplification products to form standard sequence/probe hybrids and putative sequence/probe hybrids. The respective hybrids can be differentiated using various labeling or separation schemes well known in the art and discussed below and the respective signals can be detected. Any signal associated with the putative sequence/probe hybrids can then be compared to the signal from the standard sequence/probe hybrids. In the event no signal or a diminished signal is detected from the putative sequence/probe hybrids, as compared to the signal associated with standard sequence/probe hybrids, the deletion is present. Conversely, in the case where an increased signal is detected from the putative sequence/probe hybrids, as compared to the signal associated with standard sequence/probe hybrids, a large insertion is present. It is also possible, in the above manner, to qualitatively determine the extent of the mutation to thereby determine, for example, whether a mutation is heterozygously or homozygously present in the putative sequence.

Due to the ability to detect large deletions or large insertions in the manner described above, assays for these types of variants can now be detected along with smaller variants, such as single nucleotide polymorphisms, on an automated platform using any of the well known standard labeling and detection techniques. Selection of particular labels used for detecting the amplification products by virtue of its presence on a labeled primer or probe is a matter of choice for those skilled in the art based upon the detection platform selected.

The term "label" as used herein refers to a molecule or moiety having a property or characteristic which is capable of detection. A label can be directly detectable, as with, for example, radioisotopes, fluorophores, chemiluminophores, enzymes, colloidal particles, fluorescent microparticles, fluorescence resonance energy transfer (FRET) pairs, and the like. Alternatively, a label may be indirectly detectable, as with, for example, specific binding members. It will be understood that directly detectable labels may require additional components such as, for example, substrates, triggering reagents, light, and the like to enable detection of the label. When indirect labels are used for detection, they are typically used in combination with a conjugate that generally is a specific binding member attached to a directly detectable label. As used herein, specific binding member means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; and the like.

Detection platforms that can be employed to detect the amplification products include any of the well known homogeneous or heterogeneous techniques well known in the art. Examples of homogeneous detection platforms include the use of FRET labels attached to probes that emit a signal in the presence of the target sequence. So-called TaqMan assays described in U.S. Pat. No. 5,210,015 (herein incorporated by reference) and Molecular Beacon assays described in U.S. Pat. No. 5,925,517 (herein incorporated by reference) are examples of techniques that can be employed to homogeneously detect nucleic acid sequences.

Heterogeneous formats typically employ a capture reagent to separate amplified sequences from other materials employed in the reaction. Capture reagents typically are a solid support material that is coated with one or more specific binding members specific for the same or different binding members. A "solid support material", as used herein, refers to any material which is insoluble, or can be made insoluble by a subsequent reaction. Solid support materials thus can be a latex, plastic, derivatized plastic, magnetic or non-magnetic metal, glass or silicon surface or surfaces of test tubes, microtiter wells, sheets, beads, microparticles, chips, and other configurations known to those of ordinary skill in the art. An exemplary capture reagent includes an array which generally comprises oligonucleotides or polynucleotides immobilized to a solid support material in a spatially defined manner.

Hence, a heterogeneous assay formats can be employed to detect target sequences containing large deletions or insertions, or a panel of target sequences having both single nucleotide variants and large deletions or amplifications. For example, a panel for detecting *3, *4, *5, and *6, or combinations thereof, can be performed in accordance with the methods taught in U.S. patent application Ser. No. 08/844,275, filed Apr. 18, 1997, incorporated herein by reference. In particular, primers for amplifying each of the putative target sequences can be selected, in accordance with the principles above, and combined with a test sample and amplification reagents in separate reaction vessels or the same reaction vessel to form reaction mixtures or a reaction mixture. In cases where all reagents are placed in a single reaction vessel, adjustments in the concentrations of the amplification reagents may be necessary. Adjustments for such "multiplex" reaction mixtures are well known and have been described in, for example, U.S. Pat. No. 5,582,989 (herein incorporated by reference). The reaction mixture(s) can be placed under amplification conditions to form amplification products. Probes, which may form part of the initial reaction mixture or be added in a separated step, can be hybridized to the amplification products if any to detect the presence of the various target sequences in the test samples. To facilitate detection in a heterogeneous type manner, the probes can be labeled with a first binding member which is specific for its binding partner which is attached to a solid support material such as a microparticle. Similarly, primers may be labeled with a second binding member specific for a conjugate as defined above. The amplification products bound to the probes can then be separated from the remaining reaction mixture by contacting the reaction mixture with the above solid support and then removing the solid support from the reaction mixture. Any probe/amplification product hybrids bound to the solid support may then be contacted with a conjugate to detect the presence of the hybrids on the solid support.

Many heterogeneous detection schemes for differentiating the various signals produced by the various amplification products on the solid support are available. For example, different specific binding members can be employed to bind amplification different amplification products to separate solid supports. Alternatively, all amplification products can be bound to a single solid support but different specific binding members can be employed to selectively bind distinct conjugates to the amplification products such that a different signal is associated with each of the various amplification products. It will be understood that in the event that an assay for a panel of target sequences is performed, the above techniques can be employed but would be unecessary.

Putative sequences containing large deletions, insertions, or amplifications or a panel of target sequences having both single nucleotide variants and large deletions, insertions, or amplifications can be detected using homogeneous techniques, as well. For example, a panel for detecting *3, *4, *5, and *6, or combinations thereof, can be performed in accordance with the methods taught in U.S. Pat. No. 5,925, 517, herein incorporated by reference. In particular, separate reaction mixtures containing a test sample, primers, amplification reagents and a Molecular Beacon probe for each putative target sequence can be formed in separate reaction vessels. Alternatively, all reagents necessary for amplifying and detecting the various target sequences can be formed in a single reaction vessel as in the heterogeneous type format above. The reaction mixtures (mixture) can be placed under amplification conditions to form various amplification products. The Molecular Beacon probe can then be hybridized to the various amplification products, if any. The so-formed hybrids can then be directly detected to indicate the presence a target sequence in the test sample. In cases where a single reaction mixture is formed for purposes of detecting multiple target sequences, different signal generating groups can be employed on the various Molecular Beacon probes to distinguish between the different amplification products.

Whether or not amplification products formed according to the methods herein are detected in a heterogeneous or homogeneous manner, advantageously, the products can be detected on a single apparatus. For example, the single apparatus can be any means for detecting labels associated with the amplification products such as, for example, a plate reader, spectrophotometer, and similar instruments commonly employed for detecting labels.

As noted previously, variant sequences that can be detected according to the methods provided herein can be associated with a diminished ability to metabolize drugs, an inability to metabolize drugs, or an increased ability to metabolize drugs. Hence, when such variants associated with these different abilities are detected, this information can be employed to make drug or drug dosing decisions. For example, in cases where a variant sequence associated with an inability to metabolize a particular drug or class of drugs is detected, the patient providing the test sample can be prescribed a drug that is not affected by the particular variant detected. In other cases where a variant is detected in a patients test sample that is associated with an increased or diminished metabolism for a particular drug or class of drugs, the patient can be given dosing instructions which are not inconsistent with the phenotype detected. In all cases when a test sample is from a patient the information obtained using the methods provided herein can be employed to render accurate pharmaceutical treatment regimens.

The Examples that follow illustrate preferred embodiments of the present invention and are not limiting of the claims and specification in any way.

EXAMPLES

The following examples demonstrate detection of polymorphisms in the CYP2D6 gene using the DNA oligomer primers and probes herein provided. These DNA primers and probes are identified as SEQUENCE ID NO. 2, SEQUENCE ID NO. 3, SEQUENCE ID NO. 4, SEQUENCE ID NO. 5, SEQUENCE ID NO. 6, SEQUENCE ID NO. 7, SEQUENCE ID NO. 8, SEQUENCE ID NO. 9, SEQUENCE ID NO. 10, SEQUENCE ID NO. 11, SEQUENCE ID NO. 12, SEQUENCE ID NO. 13, SEQUENCE ID NO. 14, SEQUENCE ID NO. 15, SEQUENCE ID NO. 16, SEQUENCE ID NO. 17 and SEQUENCE ID NO. 18. A portion of a representative sequence from the CYP2D6 gene is designated herein as SEQUENCE ID NO. 1.

In the following examples, SEQ ID NO. 2, SEQ ID NO. 3, SEQ ID NO. 4 and SEQ ID NO. 5 are used as amplification primers specific for portions of both the wild-type and variant CYP2D6 gene. SEQ ID NO. 2 and SEQ ID NO. 3 amplification primers are used with SEQ ID NO. 6, SEQ ID NO. 7, SEQ ID NO. 8, SEQ ID NO. 9, SEQ ID NO. 10, SEQ ID NO. 11, SEQ ID NO. 16, SEQ ID NO. 17 and SEQ ID NO. 18 internal hybridization probes. SEQ ID NO. 4 and SEQ ID NO. 5 amplification primers are used with SEQ ID NO. 12, SEQ ID NO. 13, SEQ ID NO. 14 and SEQ ID NO. 15 internal hybridization probes. SEQ ID NO. 6, SEQ ID NO. 8, SEQ ID NO. 10, SEQ ID NO. 12 and SEQ ID NO. 14 are internal hybridization probes for detecting wild-type alleles in the CYP2D6 gene amplification product. SEQ ID NO. 7, SEQ ID NO. 9, SEQ ID NO. 11, SEQ ID NO. 13, SEQ ID NO. 15, SEQ ID NO. 16, SEQ ID NO. 17 and SEQ ID NO. 18 are internal hybridization probes for detecting variant CYP2D6 gene amplification product.

Example 1

Preparation of CYP2D6 Gene Primers and Probes

A. CYP2D6 Primers

Primers were designed to bind and allow amplification of the target sequence containing both wild-type and variant alleles in the CYP2D6 gene by oligonucleotide hybridization PCR. These primers were SEQ ID NO. 2, SEQ ID NO. 3, SEQ ID NO. 4 and SEQ ID NO. 5. SEQ ID NO. 2 and SEQ ID NO. 3 are specific for a region in the CYP2D6 gene containing three polymorphisms. SEQ ID NO. 4 and SEQ ID NO. 5 are specific for a different region in the CYP2D6 gene containing another two polymorphisms. Primer sequences were synthesized using standard oligonucleotide synthesis methodology. Additionally, SEQ ID NO. 3 and SEQ ID NO. 5 were haptenated with carbazole at their 5' ends using standard cyanoethyl phosphoramidite coupling chemistry as described in U.S. Pat. No. 5,424,414 incorporated herein by reference.

B. Wild-Type and Variant CYP2D6 Probes

Probes were designed to hybridize with the amplified target sequences of wild-type or variant alleles in the CYP2D6 gene by oligonucleotide hybridization. These probes were SEQ ID NO. 6, SEQ ID NO. 8 and SEQ ID NO. 10 for the wild-type alleles, and SEQ ID NO. 7, SEQ ID NO. 9, SEQ ID NO. 11, SEQ ID NO. 16, SEQ ID NO. 17 and SEQ ID NO. 18 for the variant alleles in the region amplified by the SEQ ID NO. 2 and SEQ ID NO. 3 primers. The probes were SEQ ID NO. 12 and SEQ ID NO. 14 for the wild-type alleles, and SEQ ID NO. 13 and SEQ ID NO. 15 for the variant alleles in the region amplified by the SEQ ID NO. 4 and SEQ ID NO. 5 primers. Probe sequences were synthesized using standard oligonucleotide synthesis methodology. SEQ ID NO. 6, SEQ ID NO. 8 and SEQ ID NO. 10 were haptenated with 2 dansyls at the 5' end and blocked with phosphate at the 3' end. SEQ ID NO. 7, SEQ ID NO. 9, SEQ ID NO. 11, SEQ ID NO. 16, SEQ ID NO. 17 and SEQ ID NO. 18 were haptenated with 2 adamantanes at the 5' end and blocked with phosphate at the 3' end. SEQ ID NO. 13 and SEQ ID NO. 14 were haptenated with either 2 dansyls at the 5' end or a single dansyl, followed by 5 thymidines, another dansyl and 5 more thymidines at the 5' end, and blocked with phosphate at the 3' end. SEQ ID NO. 12 and SEQ ID NO. 15 were haptenated with either 2 adamantanes at the 5' end or a single adamantane, followed by 5 thymidines, another adamantane and 5 more thymidines at the 5' end, and blocked with phosphate at the 3' end. The probes synthesized with the poly-thymidines on the 5' end are referred to as having a poly-T linker. All syntheses used standard cyanoethyl phosphoramidite coupling chemistry as described in U.S. Pat. No. 5,464,746 (herein incorporated by reference).

Example 2

Detection of CYP2D6 Polymorphisms

DNA was isolated from whole blood using the Puregene DNA Isolation Kit (Gentra Systems, Inc., Minneapolis, Minn.) per the manufacturer's directions. The samples were genotyped by allele-specific PCR as described by Daly AK, Steen VM, Fairbrother KS and Idle JR in *Methods in Enzymology*, Vol. 272, Chapter 22 (1996), and by Wang S-L, Huang J-D, Lai M-D, Lui B-H and Lai M-L in *Clinical Pharmacology and Therapeutics*, Vol. 53, pp. 410–418 (1993). This allowed samples to be identified as either homozygous wild-type, homozygous variant or heterozygous at the five CYP2D6 polymorphisms being tested for herein.

DNA from the above samples was PCR amplified and detected using SEQ ID NO. 2 and SEQ ID NO. 3 primers with the corresponding probe pairs (wild-type or variant) for three different alleles, and using SEQ ID NO. 4 and SEQ ID NO. 5 primers with the corresponding probe pairs (wild-type or variant) for two different alleles. Each reaction mixture contained one primer pair and one probe pair (wild-type or variant) for the detection of CYP2D6 polymorphisms. The probe pairs used with the SEQ ID NO. 2 and SEQ ID NO. 3 primers were either the SEQ ID NO. 6 (wild-type) and the SEQ ID NO. 7 (variant) probes for the detection of polymorphism *2, the SEQ ID NO. 8 (wild-type) and the SEQ ID NO. 9 (variant) probes for the detection of polymorphism *3, or the the SEQ ID NO. 10 (wild-type) and the SEQ ID NO. 11 (variant) probes for the detection of polymorphism *9. The probe pairs used with the SEQ ID NO. 4 and SEQ ID NO. 5 primers were either the SEQ ID NO. 12 (wild-type) and the SEQ ID NO. 13 (variant) probes for the detection of polymorphism *4, or the SEQ ID NO. 14 (wild-type) and the SEQ ID NO. 15 (variant) probes for the detection of polymorphism *6. Primers and probes were synthesized as described above in Example 1., and the SEQ ID NO. 12, SEQ ID NO. 13, SEQ ID NO. 14 and SEQ ID NO. 15 probes used were those labeled with poly-thymidine linkers.

PCR was performed in 10×PCR buffer (GeneAmp®, Perkin Elmer, Applied Biosystems Division, Foster City, Calif.) at a final concentration of 1×, containing 10 mM Tris-HCl, pH 8.3 and 50 mM potassium chloride. Recombinant Thermus aquaticus DNA polymerase (Amplitaq®, Perkin Elmer, Applied Biosystems Division, Foster City, Calif.) was used at a concentration of 5 units/reaction, with dNTPs (dATP, dGTP, dTTP and dCTP) present at a final concentration of 200 µM each. SEQ ID NO. 2 and SEQ ID NO. 3 primers were used at a concentration of 10 nM each, and SEQ ID NO. 4 and SEQ ID NO. 5 primers were used at a concentration of 95 nM each. The final concentrations for the various probes were as follows: SEQ ID NO. 6 at 80 nM, SEQ ID NO. 7 and SEQ ID NO. 11 at 42.5 nM, SEQ ID NO. 10 at 100 nM, SEQ ID NO. 8 and SEQ ID NO. 9 at 150 nM, and SEQ ID NO. 12, SEQ ID NO. 13, SEQ ID NO. 14 and SEQ ID NO. 15 at 200 nM. A final concentration of 1.5 mM magnesium chloride (GeneAmp®, Perkin Elmer, Applied Biosystems Division, Foster City, Calif.) was also present in the reaction mixture. The total reaction volume was 0.2 ml, with a sample volume of 20 µl. The negative control consisted of the opposite allele purified DNA sample, i.e. purified variant DNA was a negative control when tested using the wild-type probe and vice versa.

Reaction mixtures were amplified in an LCx® Thermal Cycler. Reaction mixtures were first incubated at 95° C. for 2 minutes, followed by 45 cycles of PCR amplification at 95° C. for 60 seconds, 55° C. for 60 seconds then 72° C. for 60 seconds. After the reaction mixtures were thermal cycled, the mixtures were maintained at 97° C. for 5 minutes and probe oligo hybridization was accomplished by lowering the temperature to 12° C. within 2 minutes. Samples were held at 12° C. for a minimum of 5 minutes, and thereafter until reaction products were analyzed and detected.

Reaction products were detected on the Abbott LCx® system (available from Abbott Laboratories, Abbott Park, Ill.). A suspension of anti-carbazole coated microparticles, an anti-adamantane antibody/alkaline phosphatase conjugate and an anti-dansyl antibody/β-galactosidase conjugate (available from Abbott Laboratories, Abbott Park, Ill.) were used in conjunction with the LCx® to capture and detect the reaction products. The enzyme substrates used were 4-methyl-umbelliferyl phosphate (MUP) and 7-β-D-galactopyranosyloxy coumarin-4-acetic acid-(2-hydroxyethyl) amide (AUG) with the rate of conversion of substrate to product measured and reported as counts/second/second (c/s/s).

Data from this experiment is presented in TABLE 1 and shows that the wild-type probes detected both homozygous wild-type and heterozygous CYP2D6 alleles but did not detect homozygous variant CYP2D6 alleles as positive. The variant probes detected both homozygous variant and heterozygous CYP2D6 alleles but did not detect homozygous wild-type CYP2D6 alleles as positive. As expected, both probes detected the heterozygous samples since they contain one wild-type and one variant allele. Thus, all probes showed excellent specificity.

TABLE 1

| CYP2D6 Genotype | Wild-type probe LCx ® rate | Variant probe LCx ® rate |
| --- | --- | --- |
| *2 - Homozygous wild-type | 1223.0 | 145.6 |
| *2 - Heterozygous | 819.3 | 449.6 |
| *2 - Homozygous variant | 107.1 | 811.0 |
| *3 - Homozygous wild-type | 671.6 | 83.0 |
| *3 - Heterozygous | 521.7 | 229.6 |
| *9 - Homozygous wild-type | 1539.1 | 81.0 |
| *9 - Homozygous variant | 99.9 | 811.7 |
| *4 - Homozygous wild-type | 390.2 | 75.5 |
| *4 - Heterozygous | 236.4 | 412.0 |

TABLE 1-continued

| CYP2D6 Genotype | Wild-type probe LCx ® rate | Variant probe LCx ® rate |
|---|---|---|
| *4 - Homozygous variant | 57.5 | 549.6 |
| *6 - Homozygous wild-type | 1151.7 | 81.8 |
| *6 - Heterozygous | 962.8 | 208.7 |

Example 3

Probes with and without Poly-Thymidine Linkers

Selected purified DNA samples, prepared as in Example 2., were tested for polymorphisms *4 and *6 using wild-type and variant probes with and without poly-thymidine (poly-T) linkers. These probes were SEQ ID NO. 12, SEQ ID NO. 13, SEQ ID NO. 14 and SEQ ID NO. 15 prepared as described in Example 1, with or without poly-T at the 5' ends interspersed with the hapten groups. Samples were PCR amplified and detected using these probes with SEQ ID NO. 4 and SEQ ID NO. 5 primers as described in Example 2. All samples were tested in duplicate.

The average of the results from this experiment is given in Table 2. These results show that the probes with the poly-T linker had a higher signal than the probes without the linker.

TABLE 2

| CYP2D6 Genotype | Probe with Poly-T linker | | Probe without Poly-T linker | |
|---|---|---|---|---|
| | Wild-type LCx ® rate | Variant LCx ® rate | Wild-type LCx ® rate | Variant LCx ® rate |
| *4-Homozygous wild-type | 433.9 | 145.1 | 313.0 | 186.1 |
| *4-Homozygous variant | 90.5 | 1291.9 | 40.4 | 838.7 |
| *6-Homozygous wild-type | 1461.6 | 100.0 | 937.5 | 50.8 |
| *6-Heterozygous | 1130.4 | 272.5 | 603.7 | 119.0 |

Example 4

Effect of Probe Length on *2 Detection

The effect of probe length on allele detection was tested using the adamantane labeled probe for detection of the variant *2. Probe lengths tested were an 11 mer (SEQ ID NO. 16), a 13 mer (SEQ ID NO. 7), a 15 mer (SEQ ID NO. 17) and a 17 mer (SEQ ID NO. 18).

DNA was purified from samples genotyped as wild-type or variant for *2 as in Example 2. Single replicates of these samples were PCR amplified and detected as in Example 2. using SEQ ID NO. 2 and SEQ ID NO. 3 primers with one of the four lengths of labeled mutant probes in each reaction mixture.

The results, shown below in Table 3, indicate that the optimum probe length is a 13 mer, with the mismatch between the variant and wild-type allele occurring at position 7. A shorter probe length (the 11 mer) was not able to hybridize well to the variant target, resulting in a signal barely above the background for the mismatched (wild-type) DNA. While longer probe lengths (the 15 mer and 17 mer) did hybridize to the matching target, they also showed higher backgrounds with the mismatched target. Thus, the longer the probe (over the 13 mer optimal length), the worse the discrimination for a target with a single base mismatch.

TABLE 3

| | Length of Variant Probe LCx ® rate (c/s/s) | | | |
|---|---|---|---|---|
| Sample | 11mer | 13mer | 15mer | 17mer |
| Variant (Matched) DNA | 111.5 | 647.3 | 914.2 | 481.8 |
| Wild-type (Mis-matched) DNA | 90.9 | 79.6 | 340.6 | 417.0 |

Example 5

Detection of Heterozygous Carriers of *5

In this example, the *5 mutation is detected in human blood samples that were heterozygous for *5 mutation or are homozygous for the non-variant sequence. The genotypes of the samples were determined using allele-specific PCR and long PCR.

The primer and probe selections were based upon sequences for CYP2D6, CYP2D7P, and CYP2D*5 having respective GenBank accession numbers M33388, M33387, and X90927. Specifically, one forward primer was specific for CYP2D6 (SEQ ID NO. 19) and another forward primer (SEQ ID NO. 20) was specific for a psuedogene of CYP2D6, namely CYP2D7P. A reverse primer (SEQ ID NO. 21) was common for both the CYP2D6 and CYP2D7P target sequences insofar as it participates in the amplification of both sequences. SEQ ID NO. 22 is a Molecular Beacon labeled at its 5' end with fluorescein and dabcyl at its 3' end. SEQ ID NO. 22 (in the region which is not self complementary) is perfectly complementary to the CYP2D6 amplification product and has a single base pair mismatch with the CYP2D7P amplification product. Another, unlabeled Molecular Beacon probe (SEQ ID NO. 23) was (in the region that is not self complementary) perfectly complementary to the CYP2D7P amplification product. SEQ ID NO. 23 was used for purposes of providing a competitive probe for the CYP2D7P amplification product. The primers and Molecular Beacons were synthesized using standard cyanoethyl phosphoramidite chemistry as described in U.S. Pat. No. 5,464,746, herein incorporated by reference.

The amplification reaction and detection of the amplification product was run in a unit dose format and read in real-time (i.e. after each amplification cycle) using a Perkin-Elmer 7700 thermocycler. Reagents for amplification and detection were placed in a single reaction vessel for cycling and detection. In particular, each 50 µl reaction contained 1× Gibco BRL PCR buffer (Gibco, Inc.; Grand Island, NY), 1.5 mM magnesium chloride, 0.2 mM dNTPs, 2.5 units of Gibco BRL Platinum Taq polymerase, 0.1 µM of each primer, 0.1 µM of each probe, 12.5 ng of genomic sample DNA, and 0.15 µl of Texas-Red conjugated heptanucleotide control. Samples were obtained from Interstate Blood Bank, Inc. (Chicago, Ill.)

Individual reaction vessels were placed in the thermocycler and 45 cycles of the following was performed: 60 seconds at 94° C., 20 seconds at 59° C., 40 seconds at 61° C., and 40 seconds at 72° C. A fluorescent reading was taken at the 61° C. step of each cycle.

Sample designations along with the cycle number at which a fluorescent reading was detectable over a given threshold value (Ct) are shown in Table 4. Samples designated A1, B1, C1, D1, and E1 were heterozygous for *5. All other samples did not contain *5. As seen from the data, signals from samples containing *5 were consistently detected in later cycles than samples that did not contain *5 largely because the samples lacking *5 contained a greater proportion of target sequence for amplification.

TABLE 4

| Sample Designation | Ct |
| --- | --- |
| A1 | 34 |
| A2 | 32 |

TABLE 4-continued

| Sample Designation | Ct |
| --- | --- |
| B1 | 36 |
| B2 | 30 |
| C1 | 36 |
| C2 | 31 |
| D1 | 34 |
| D2 | 30 |
| E1 | 33 |
| E2 | 31 |
| F1 | 30 |
| F2 | 29 |
| G1 | 29 |
| G2 | 30 |
| H1 | 30 |

While the invention has been described in detail and with reference to specific embodiments, it will be apparent to one skilled in the art that various changes and modifications may be made to such embodiments without departing from the spirit and scope of the invention.

What is claimed is:

1. A method for detecting a target nucleic acid sequence suspected of having single or large deletions or insertions in a test sample comprising the steps of:
   a) contacting the test sample with amplification reagents comprising a polymerase, a primer pair, and a probe to form a reaction mixture;
   b) performing the following cycle comprising the steps of:
      (i) maintaining the reaction mixture for a time and at temperature above 90° C., sufficient to dissociate double stranded nucleic acid sequences,
      (ii) maintaining the reaction mixture for a time and at a temperature from 45° C. to 65° C. to allow the primers and probe to hybridize to the nucleic acid and thereby form primer hybrids and probe hybrids,
      (iii) maintaining the reaction mixture for a time and at a temperature at least 1° C. above the temperature in (ii), sufficient to dissociate the probe hybrids, if the probe is not completely complementary to the nucleic acid, and
      (iv) raising the temperature of the reaction mixture to a temperature sufficient to activate the polymerase;
   c) repeatedly performing the cycle of step b) to form an amplification product; and
   d) detecting the amplification product as an indication of the presence of the nucleic acid sequence in the test sample.

2. The method of claim 1 wherein the target nucleic acid sequence is a polymorphic nucleic acid sequence.

3. A method for determining whether a deletion or insertion of at least 50 base pairs is present in DNA in a test sample comprising the steps of
   a) contacting the test sample with amplification reagents wherein the amplification reagents comprise amplification primers, a probe and a polymerase, to form a reaction mixture in which one of the amplification primers hybridize with the target nucleic acid and a standard nucleic acid sequence in the test sample;
   b) subjecting the reaction mixture to amplification conditions to form a target nucleic acid sequence amplification product and a standard nucleic acid amplification product, wherein the amplification conditions comprise performing the following cycle comprising the steps of:
      (i) maintaining the reaction mixture for a time and at temperature above 90° C., sufficient to dissociate double stranded DNA sequences,
      (ii) maintaining the reaction mixture for a time and at a temperature from 45° C. to 65° C. to allow the amplification primers and probe to hybridize to the DNA and thereby form primer hybrids and probe hybrids,
      (iii) maintaining the reaction mixture for a time and at a temperature at least 1° C. above the temperature in (ii) sufficient to dissociate the probe hybrids, if the probe is not completely complementary to the DNA,
      (iv) raising the temperature of the reaction mixture to a temperature sufficient to activate the polymerase;

c) detecting a first signal that is proportional to the amount of the target nucleic acid sequence amplification product;
d) detecting a second signal that is proportional to the amount of the standard nucleic acid amplification product; and
e) comparing the first and second signal to determine whether a deletion or insertion of at least 50 base pairs is present in the DNA in the test sample.

4. The method of claim 3 wherein the deletion or insertion is of at least 200 base pairs.

5. The method of claim 3 wherein the deletion or insertion is of at least 1000 base pairs.

6. The method of claim 3 wherein the insertion or deletion is in the CYP2D6 locus.

* * * * *

SEQUENCE LISTING

<160> NUMBER OF SEQ ID NOS: 23

<210> SEQ ID NO 1
<211> LENGTH: 1450
<212> TYPE: DNA
<213> ORGANISM: Homo sapiens

<400> SEQUENCE: 1

```
tagggttgga gtgggtggtg gatggtgggg ctaatgcctt catggccacg cgcacgtgcc      60
cgtcccaccc ccagggtgt tcctggcgcg ctatgggccc gcgtggcgcg agcagaggcg     120
cttctccgtg tccaccttgc gcaacttggg cctgggcaag aagtcgctgg agcagtgggt    180
gaccgaggag gccgcctgcc tttgtgccgc cttcgccaac cactccggtg ggtgatgggc    240
agaagggcac aaagcgggaa ctgggaaggc ggggacggg gaaggcgacc ccttacccgc     300
atctcccacc cccaggacgc ccctttcgcc ccaacggtct cttggacaaa gccgtgagca    360
acgtgatcgc ctccctcacc tgcgggcgcc gcttcgagta cgacgaccct cgcttcctca    420
ggctgctgga cctagctcag gagggactga aggaggagtc gggctttctg cgcgaggtgc    480
ggagcgagag accgaggagt ctctgcaggg cgagctcccg agaggtgccg gggctggact    540
ggggcctcgg aagagcagga tttgcataga tgggtttggg aaaggacatt ccaggagacc    600
ccactgtaag aagggcctgg aggaggaggg gacatctcag acatggtcgt gggagaggtg    660
tgcccgggtc aggggggcacc aggagaggcc aaggactctg tacctcctat ccacgtcaga    720
gatttcgatt ttaggttttct cctctgggca aggagagagg gtggaggctg gcacttgggg    780
agggacttgg tgaggtcagt ggtaaggaca ggcaggccct gggtctacct ggagatggct    840
ggggcctgag acttgtccag gtgaacgcag agcacaggag ggattgagac cccgttctgt    900
ctggtgtagg tgctgaatgc tgtccccgtc ctcctgcata tcccagcgct ggctggcaag    960
gtcctacgct tccaaaaggc tttcctgacc cagctggatg agctgctaac tgagcacagg   1020
atgacctggg acccagccca gcccccccga gacctgactg aggccttcct ggcagagatg   1080
```

```
gagaaggtga gagtggctgc cacggtgggg ggcaagggtg gtgggttgag cgtcccagga    1140
ggaatgaggg gaggctgggc aaaaggttgg accagtgcat cacccggcga gccgcatctg    1200
ggctgacagg tgcagaattg gaggtcattt gggggctacc ccgttctgtc ccgagtatgc    1260
tctcggccct gctcaggcca aggggaaccc tgagagcagc ttcaatgatg agaacctgcg    1320
catagtggtg gctgacctgt tctctgccgg gatggtgacc acctcgacca cgctggcctg    1380
gggcctcctg ctcatgatcc tacatccgga tgtgcagcgt gagcccatct gggaaacagt    1440
gcaggggccg                                                           1450

<210> SEQ ID NO 2
<211> LENGTH: 20
<212> TYPE: DNA
<213> ORGANISM: Artificial Sequence
<220> FEATURE:
<223> OTHER INFORMATION: Amplication Primer

<400> SEQUENCE: 2
tgagacttgt ccaggtgaac                                                  20

<210> SEQ ID NO 3
<211> LENGTH: 18
<212> TYPE: DNA
<213> ORGANISM: Artificial Sequence
<220> FEATURE:
<223> OTHER INFORMATION: Amplication Primer

<400> SEQUENCE: 3
cctgcactgt ttcccaga                                                    18

<210> SEQ ID NO 4
<211> LENGTH: 18
<212> TYPE: DNA
<213> ORGANISM: Artificial Sequence
<220> FEATURE:
<223> OTHER INFORMATION: Amplication Primer

<400> SEQUENCE: 4
gtggatggtg gggctaat                                                    18

<210> SEQ ID NO 5
<211> LENGTH: 18
<212> TYPE: DNA
<213> ORGANISM: Artificial Sequence
<220> FEATURE:
<223> OTHER INFORMATION: Amplication Primer

<400> SEQUENCE: 5
ctcctcggtc tctcgctc                                                    18

<210> SEQ ID NO 6
<211> LENGTH: 13
<212> TYPE: DNA
<213> ORGANISM: Artificial Sequence
<220> FEATURE:
<223> OTHER INFORMATION: Probe

<400> SEQUENCE: 6
aacctgcgca tag                                                         13

<210> SEQ ID NO 7
<211> LENGTH: 13
<212> TYPE: DNA
<213> ORGANISM: Artificial Sequence
```

-continued

```
<220> FEATURE:
<223> OTHER INFORMATION: Probe

<400> SEQUENCE: 7
aacctgtgca tag                                                        13

<210> SEQ ID NO 8
<211> LENGTH: 13
<212> TYPE: DNA
<213> ORGANISM: Artificial Sequence
<220> FEATURE:
<223> OTHER INFORMATION: Probe

<400> SEQUENCE: 8
gagcacagga tga                                                        13

<210> SEQ ID NO 9
<211> LENGTH: 13
<212> TYPE: DNA
<213> ORGANISM: Artificial Sequence
<220> FEATURE:
<223> OTHER INFORMATION: Probe

<400> SEQUENCE: 9
gagcacggat gac                                                        13

<210> SEQ ID NO 10
<211> LENGTH: 14
<212> TYPE: DNA
<213> ORGANISM: Artificial Sequence
<220> FEATURE:
<223> OTHER INFORMATION: Probe

<400> SEQUENCE: 10
gatggagaag gtga                                                       14

<210> SEQ ID NO 11
<211> LENGTH: 14
<212> TYPE: DNA
<213> ORGANISM: Artificial Sequence
<220> FEATURE:
<223> OTHER INFORMATION: Probe

<400> SEQUENCE: 11
gatggaggtg agag                                                       14

<210> SEQ ID NO 12
<211> LENGTH: 13
<212> TYPE: DNA
<213> ORGANISM: Artificial Sequence
<220> FEATURE:
<223> OTHER INFORMATION: Probe

<400> SEQUENCE: 12
ccccaggacg ccc                                                        13

<210> SEQ ID NO 13
<211> LENGTH: 13
<212> TYPE: DNA
<213> ORGANISM: Artificial Sequence
<220> FEATURE:
<223> OTHER INFORMATION: Probe

<400> SEQUENCE: 13
ccccaagacg ccc                                                        13
```

```
<210> SEQ ID NO 14
<211> LENGTH: 14
<212> TYPE: DNA
<213> ORGANISM: Artificial Sequence
<220> FEATURE:
<223> OTHER INFORMATION: Probe

<400> SEQUENCE: 14
gagcagtggg tgac                                                      14

<210> SEQ ID NO 15
<211> LENGTH: 14
<212> TYPE: DNA
<213> ORGANISM: Artificial Sequence
<220> FEATURE:
<223> OTHER INFORMATION: Probe

<400> SEQUENCE: 15
gagcaggggt gacc                                                      14

<210> SEQ ID NO 16
<211> LENGTH: 11
<212> TYPE: DNA
<213> ORGANISM: Artificial Sequence
<220> FEATURE:
<223> OTHER INFORMATION: Probe

<400> SEQUENCE: 16
acctgtgcat a                                                         11

<210> SEQ ID NO 17
<211> LENGTH: 15
<212> TYPE: DNA
<213> ORGANISM: Artificial Sequence
<220> FEATURE:
<223> OTHER INFORMATION: Probe

<400> SEQUENCE: 17
gaacctgtgc atagt                                                     15

<210> SEQ ID NO 18
<211> LENGTH: 17
<212> TYPE: DNA
<213> ORGANISM: Artificial Sequence
<220> FEATURE:
<223> OTHER INFORMATION: Probe

<400> SEQUENCE: 18
agaacctgtg catagtg                                                   17

<210> SEQ ID NO 19
<211> LENGTH: 21
<212> TYPE: DNA
<213> ORGANISM: Artificial Sequence
<220> FEATURE:
<223> OTHER INFORMATION: Forward Primer

<400> SEQUENCE: 19
ccccaaaacg gaagacaaat c                                              21

<210> SEQ ID NO 20
<211> LENGTH: 15
<212> TYPE: DNA
<213> ORGANISM: Artificial Sequence
<220> FEATURE:
<223> OTHER INFORMATION: Forward Primer
```

```
-continued

<400> SEQUENCE: 20
tcccgcacac gcctc                                                      15

<210> SEQ ID NO 21
<211> LENGTH: 19
<212> TYPE: DNA
<213> ORGANISM: Artificial Sequence
<220> FEATURE:
<223> OTHER INFORMATION: Reverse Primer

<400> SEQUENCE: 21
tgcgaactcg tcactggtc                                                  19

<210> SEQ ID NO 22
<211> LENGTH: 35
<212> TYPE: DNA
<213> ORGANISM: Artificial Sequence
<220> FEATURE:
<223> OTHER INFORMATION: Molecular Beacon Probe

<400> SEQUENCE: 22
ccgcacacag gactggctac ctctctgggc tgcgg                                35

<210> SEQ ID NO 23
<211> LENGTH: 31
<212> TYPE: DNA
<213> ORGANISM: Artificial Sequence
<220> FEATURE:
<223> OTHER INFORMATION: Molecular Beacon Probe

<400> SEQUENCE: 23
cgaccacagg actggccacc tctctgggtc g                                    31
```